United States Patent

Uchida et al.

Patent Number: 5,196,567
Date of Patent: Mar. 23, 1993

[54] BIPHENYLYLPROPIONIC ACID DERIVATIVE, PROCESS FOR PREPARING THE SAME AND PHARMACEUTICAL COMPOSITION CONTAINING THE SAME

[75] Inventors: Katsuhiro Uchida, Kyoto; Shozo Masumoto, Shiga; Masao Tohno; Mitsuo Mimura, both of Otsu; Makoto Okumura, Moriyama, all of Japan

[73] Assignee: Kaken Pharmaceutical Co., Ltd., Tokyo, Japan

[21] Appl. No.: 204,313

[22] Filed: Jun. 9, 1988

Related U.S. Application Data

[60] Division of Ser. No. 742,147, Jun. 7, 1985, Pat. No. 4,766,148, which is a continuation of Ser. No. 531,378, Sep. 12, 1983, abandoned.

[30] Foreign Application Priority Data

Feb. 19, 1983 [JP] Japan .................. 58-26559

[51] Int. Cl.$^5$ .............................. C07C 69/76
[52] U.S. Cl. ...................................... 560/102
[58] Field of Search ........................ 560/102

[56] References Cited

U.S. PATENT DOCUMENTS

| 1,345,628 | 12/1971 | Pfister . | |
| 2,518,922 | 6/1946 | Mowry | 260/388 |
| 3,752,844 | 8/1973 | Pfister | 260/470 |
| 3,755,427 | 8/1973 | Adams et al. | 260/515 |
| 3,932,499 | 1/1976 | Adams et al. | 260/515 |
| 4,256,760 | 3/1981 | Los | 424/279 |
| 4,271,188 | 6/1981 | Hindley | 424/309 |
| 4,309,420 | 1/1982 | Ghyezy et al. | 424/199 |
| 4,324,904 | 4/1982 | Hylton et al. | 560/102 |
| 4,613,505 | 9/1986 | Mizushima | 424/80 |

FOREIGN PATENT DOCUMENTS

| 1148166 | 1/1983 | Canada . |
| 103265 | 3/1984 | European Pat. Off. . |
| 129435 | 12/1984 | European Pat. Off. . |
| 56-45467 | 4/1981 | Japan . |
| 60-16923 | 1/1985 | Japan . |

OTHER PUBLICATIONS

Baldwin et al, *Eur. J. Med. Chem.—Chim. Ther.*, 17, 297(1982).

*Primary Examiner*—Paul J. Killos
*Attorney, Agent, or Firm*—Armstrong, Westerman, Hattori, McLeland & Naughton

[57] ABSTRACT

Biphenylylpropionic acid derivatives of the formula:

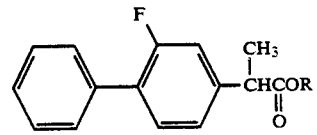

wherein R is an alkylcarbonyloxyalkyl group or an alkenylcarbonyloxyalkyl group having the formula:

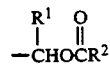

wherein $R^1$ is a lower alkyl group having 1 to 5 carbon atoms and $R^2$ is an alkyl group having 1 to 15 carbon atoms or an alkenyl group having 2 to 8 carbon atoms, or a lactone having the formula:

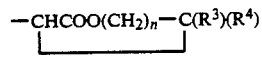

wherein $R^3$ and $R^4$ are hydrogen atom or a lower alkyl group having 1 to 2 carbon atoms, and n is an integer of 1 or 2. The compounds have excellent anti-inflammatory, analgesic and antipyretic activities. Moreover, the compounds have no irritation, rapid and long-acting, and high safety margin.

4 Claims, No Drawings

BIPHENYLYLPROPIONIC ACID DERIVATIVE, PROCESS FOR PREPARING THE SAME AND PHARMACEUTICAL COMPOSITION CONTAINING THE SAME

This is a division of application Ser. No. 742,147, U.S. Pat. No. 4,766,148 filed Jun. 7, 1985, which is a continuation of Ser. No. 531,378 filed Sep. 12, 1983 now abandoned.

BACKGROUND OF THE INVENTION

The present invention relates to novel biphenylyl propionic acid derivatives. More particularly, the present invention relates to biphenylylpropionic acid derivatives having the formula (I):

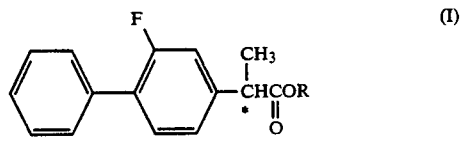

wherein R is an alkylcarbonyloxyalkyl group or an alkenylcarbonyloxyalkyl group having the formula (II):

wherein $R^1$ is a lower alkyl group having 1 to 5 carbon atoms and $R^2$ is an alkyl group having 1 to 15 carbon atoms or an alkenyl group having 2 to 8 carbon atoms, or a lactone having the formula (III):

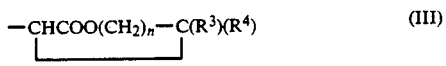

wherein $R^3$ and $R^4$ are hydrogen atom or a lower alkyl group having 1 to 2 carbon atoms, and n is an integer of 1 or 2, a process for preparing the same and a pharmaceutical composition containing the same as an effective ingredient.

It is known that 2-(2-fluoro-4-biphenylyl)-propionic acid (hereinafter referred to as "FP") has strong anti-inflammatory, analgesic and antipyretic activities. However, the formulation form of FP is limited in the form of injection, syrup, or an external preparation such as ophthalmic agent, suppository, cream or plaster because of its irritation. Thus, various modifications are required for a pharmaceutical preparation of FP and the preparation is difficult.

As a result of various studies, the present inventors have now found that a satisfactory drug which causes no irritation, and excellent pharmacological effect several times higher than that of FP and fewer side effects. That is, the compound (I) of the present invention prepared from FP by esterifying causes no irritation. Moreover, the compound (I) is excellent in absorption from mucosa or skin because of its high hydrophobic property. Thus, the pharmacological effect of the compound (I) is appears rapidly and is increased. On the other hand, when the compound (I) is formulated in combination with an oleaginous base, the pharmacological effect of the compound (I) is increased and prolonged, and the bioavailability of the compound (I) is increased. Further, the compound (I) is hard to bind with plasma proteins because of its physicochemical properties such as no free polar group and solubility in oil. As a result, the tissue distribution and metabolism of the compound (I) after administration are different from those of FP. Accordingly, the concentration of the compound (I) at an inflammatory site is increased to show excellent pharmacological effects.

Through a substained-release agent is generally utilized in order to prolong a pharmacological effect, the compound (I) of the present invention gains a prolongation of a pharmacological effect by advantageously utilizing a reaction of metabolic enzyme. More particularly, since the compound (I) has diastereomers as a result of having two asymmetric carbon atoms in the molecular, there is evidenced a difference of hydrolyzing rate among the diastereomers when the compound (I) is hydrolyzed by metabolic enzymes in tissues. When measured by gas chromatography, for instance, there appears about 5-fold difference in the hydrolyzing rate in plasma. Thus, FP being a parent material of the compound (I) is slowly and complementarily released in its physiologically active form in tissues to prolong an effective blood concentration of FP.

Therefore, the compound (I) is excellent as a drug causing no irritation, excellent pharmacological effect, rapid and long-acting and has a large safety margin.

It is an object of the present invention to provide novel FP derivatives which are useful and characteristic pro-drugs by utilizing advantageously an enzyme reaction. The compounds have excellent anti-inflammatory, analgesic and antipyretic activities, fewer side effects and high safety.

A further object of the invention is to provide a process for preparing FP derivatives.

Another object of the invention is to provide a pharmaceutical composition containing FP derivatives as effective ingredients.

These and other objects of the invention will become apparent from the description hereinafter.

SUMMARY OF THE INVENTION

In accordance with the present invention, there can be provided a FP derivative having the formula (I):

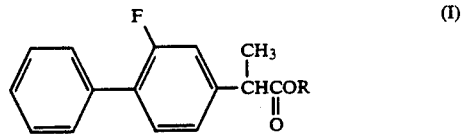

wherein R is an alkylcarbonyloxyalkyl group or an alkenylcarbonyloxyalkyl group having the formula (II):

wherein $R^1$ is a lower alkyl group having 1 to 5 carbon atoms and $R^2$ is an alkyl group having 1 to 15 carbon atoms or an alkenyl group having 2 to 8 carbon atoms, or a lactone having the formula (III):

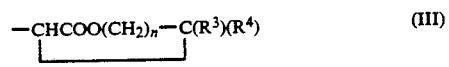

wherein $R^3$ and $R^4$ are hydrogen atom or a lower alkyl group having 1 to 2 carbon atoms, and n is an integer of 1 or 2.

DETAILED DESCRIPTION OF THE INVENTION

The preferable substituent group defined as R in the formula (I) is 1-acetoxyethyl, 1-acetoxypropyl, 1-propionyloxyethyl, 1-isobutyryloxyethyl, 1-pivaloyloxyethyl, 1-palmitoyloxyethyl, 1-crotonoyloxyethyl, 1-(3,3-dimethylacryloyloxy)ethyl, 1-(2,4-hexadienoyloxy)ethyl or 3,3-dimethyl-γ-butyrolactone-2-yl group.

Representative compounds among the FP derivatives (I) are as follows:

| | |
|---|---|
| Compound No. 1: | 1-(acetoxy)ethyl 2-(2-fluoro-4-biphenylyl)-propionate |
| Compound No. 2: | 1-(propionyloxy)ethyl 2-(2-fluoro-4-biphenylyl)propionate |
| Compound No. 3: | 1-(isobutyryloxy)ethyl 2-(2-fluoro-4-biphenylyl)propionate |
| Compound No. 4: | 1-(pivaloyloxy)ethyl 2-(2-fluoro-4-biphenylyl)propionate |
| Compound No. 5: | 1-(palmitoyloxy)ethyl 2-(2-fluoro-4-biphenylyl)propionate |
| Compound No. 6: | 1-(acetoxy)propyl 2-(2-fluoro-4-biphenylyl)-propionate |
| Compound No. 7: | 1-(crotonoyloxy)ethyl 2-(2-fluoro-4-biphenylyl)propionate |
| Compound No. 8: | [1-(3,3-dimethylacryloyloxy)ethyl] 2-(2-fluoro-4-biphenylyl)propionate |
| Compound No. 9: | [1-(2,4-hexadienoyloxy)ethyl] 2-(2-fluoro-4-biphenylyl)propionate |
| Compound No. 10: | 3,3-dimethyl-2-[2-(2-fluoro-4-biphenylyl)-propionyloxy]-γ-butyrolactone |

The FP derivatives (I) of the present invention are prepared by reacting FP or the salt thereof having the formula (IV):

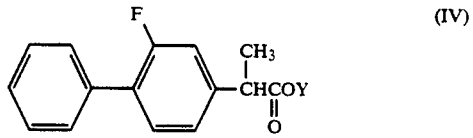
(IV)

wherein Y is hydrogen atom or a metal salt, with a compound having the formula (V):

(V)

wherein $R^1$ and $R^2$ are as defined above and X is a halogen atom, or a compound having the formula (VI):

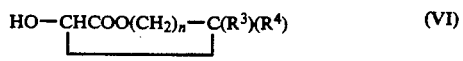
(VI)

wherein $R^3$, $R^4$ and n are as defined above.

Though the above reactions can be conducted by employing any conventional esterifying reaction, the following method is preferred in point of yield and industrial production.

That is, the esterifying reaction between FP or the salt thereof having the formula (IV) and a compound (V) is generally carried out in an aprotic organic solvent such as N,N-dimethylformamide, dimethylsulfoxide or hexamethylsulfonyltriamide, or an organic solvent such as acetonitrile, dichloromethane, dichloroethane, chloroform, benzene, ether or tetrahydrofuran, and in the presence or absence of an alkali metal carbonate such as sodium carbonate, potassium carbonate, sodium bicarbonate or potassium bicarbonate, an alkali hydroxide such as sodium hydroxide or potassium hydroxide, an alkali metal hydride such as sodium hydride, potassium hydride or lithium hydride, an organic base such as pyridine, triethylamine, N,N-dimethylaniline or tetramethylethylenediamine, an alkali metal iodide such as sodium iodide or potassium iodide, or a phase transfer catalyst such as a crown ether, e.g. 15-crown-5 or 18-crown-6, [2,2,2]-cryptand or [2,2,2]-benzocryptand.

Examples of the salt of the compound (IV) employed in the above reaction are, for instance, metal salts such as silver and copper salt, alkali metal salts such as lithium, sodium and potassium salts. The above-mentioned aprotic organic solvents may be also employed in combination with ether, tetrahydrofuran, benzene, chloroform, dichloromethane, dichloroethane or acetone.

On the other hand, the esterifying reaction between a FP derivative (IV) and an alcohol derivative (VI) is carried out by dehydration condensation in an organic solvent, under neutral condition and in the absence or presence of a catalyst or a dehydrating agent.

Suitable examples of the organic solvent employed in the above reaction are, for instance, dichloromethane, chloroform, ether, benzene, tetrahydrofuran, and the like. Examples of the dehydrating agent employed in the above reaction are, for instance, N,N-dicyclohexylcarbodiimide, 1-ethyl-(3,3-dimethylaminopropyl)carbodiimide (water soluble carbodiimide), their hydrochlorides, and the like. Examples of the catalyst employed in the above reaction are, for instance, pyridine, halogenopyridine, tributylamine, aminopyridine, p-dimethylaminopyridine, and the like. The use of p-dimethylaminopyridine produces a particularly high yield.

As one of the applications of an active esterifying reaction, the desired compound (I) may be prepared by reacting an imidazoate obtained by reacting a FP derivative (IV) with carbonyldiimidazole, with the above alcohol derivative (VI). The desired compound (I) may be also prepared in a high yield by dehydration condensation conducted by using triphenylphosphin or triethyl phosfite and an azodicarboxylic acid dialkyl ester.

The amounts of the compounds (V) or (VI) to be used in the above reactions are usually employed in an amount not less than 1.0 mole, preferably 1.0 to 1.5 moles, per mole of the compound (IV).

The reaction temperature is not particularly limited, but the reaction is usually carried out at a temperature of 0° to 120° C. Though the reaction time is varied depending on the reaction conditions such as kinds of solvent or catalyst and temperature, the reaction is usually carried out for several minutes to more than ten hours.

The FP derivatives (I) of the present invention have excellent anti-inflammatory, analgesic and antipyretic activities, and also a high degree of biological hydrolysis. Particularly, 1-(acetoxy)ethyl 2-(2-fluoro-4-biphenylyl)propionate, 1-(propionyloxy)ethyl 2-(2-fluoro-4-biphenylyl)propionate, 1-(crotonoyloxy) ethyl 2-(2-fluoro-4-biphenylyl)propionate and 3,3-dimethyl 2-[2-(2-fluoro-4-biphenylyl)propionyloxy]-γ-butyrolactone show excellent pharmacological effects. Accordingly, the FP derivatives (I) are very useful as anti-inflammatory, analgestic, antipyretic and anti-rhematoid agents. They can be formulated in a usual manner into compositions in the form of tablet, suppository, cream and capsule with conventional pharmaceutical carriers. Any conventional carriers used in preparations can be employed in the present invention. Examples of the carrier are, for instance, excipients, binders, lubricants, coloring agents, perfumes, emulsifying agents dispersing agents, sterilized water, plant oil, harmless organic solvent, and the like.

With respect to the representative compounds of the present invention (the above Compound Nos. 1 to 10), the results of $ED_{50}$ (50% effective dose) orally or intravenously in rats by a carrageenan-induced edema inhibitory test, $UD_{50}$ (50% ulcerative dose) orally in rats by a gastric irritation test, hydrolyzing rate in human plasma (incubation at 37° C. for one hour) and $LD_{50}$ (50% lethal dose) orally in mice are shown in Table 1.

TABLE 1

| | Compound No. | $ED_{50}$ mg./kg. p.o. | $ED_{50}$ mg./kg. i.v. | $UD_{50}$ mg./kg. p.o. | Hydrolyzing rate (%) | $LD_{50}$ mg./kg. p.o. |
|---|---|---|---|---|---|---|
| Compounds of the invention | 1 | 0.5 | 0.05 | 2.5 | 70.7 | 650 |
| | 2 | 0.7 | 0.06 | 3.0 | 56.3 | 800 |
| | 3 | 1.5 | 0.1 | 5.0 | 35.2 | 880 |
| | 4 | 2.5 | 0.6 | 10.0 | 8.3 | >1000 |
| | 5 | >5.0 | >5.0 | >10.0 | 2.0 | >1000 |
| | 6 | 1.5 | 0.1 | 5.0 | 36.0 | 900 |
| | 7 | 0.9 | 0.08 | 4.0 | 42.0 | 800 |
| | 8 | 2.5 | 0.3 | 7.0 | 19.8 | 1000 |
| | 9 | 2.0 | 0.3 | 7.0 | 20.4 | 1000 |
| | 10 | 0.5 | 0.05 | 2.5 | 72.3 | 670 |
| Comparative compounds | acemethacin | 8.3 | — | 17.5 | 4.2 | 18.0 |
| | indomethacin | 5.5 | 1.25 | 5.0 | — | 14.0 |
| | FP | 0.8 | 0.3 | 1.0 | — | 440 |

As is clear from Table 1, the compounds (I) of the present invention have excellent pharmacological effects in comparison with the comparative compounds such as acemethacin, indomethacin and FP. For example, the carrageenan-induced edema inhibitory effect of the compound (I) is about 8 times that of indomethacin and the same as that of FP. Especially, in case of intravenously administration, the activity of the compound (I) is about 6 times that of FP and 25 times that of indomethacin. With respect to ulceration of gastrointestinal tract which is one of the main side effects of anti-inflammatory agents, the ulcerative effect of the compound (I) is about one third that of FP. $LD_{50}$ of the compound (I) is 1.5 to 2.0 times higher than that of FP. Thus, the acute toxicity of the compounds (I) is considerably reduced. Furthermore, the safety margin of the compound (I) expressed by a ratio of $UD_{50}$ to $ED_{50}$ is about 3 times broader than that of FP.

The present invention is more particularly described and explained by means of the following Examples, in which all % are by weight unless otherwise noted. In order to illustrate the preparation of (1-chloroethyl)crotonate, (1-chloroethyl)-3,3-dimethylacrylate and (1-chloroethyl)-2,4-hexadienoate employed as starting materials for preparing the FP derivatives (I) of the invention, the following Reference Examples are also presented.

REFERENCE EXAMPLE 1

(1-Chloroethyl)crotonate

Into a reaction vessel were added 4.8 g. of paraldehyde and 0.14 g. of 96% zinc chloride. To the resulting mixture was added dropwise 10.5 g. (0.1 mole) of crotonoyl chloride with ice-cooling, and then the reaction mixture was reacted with stirring at a room temperature for 2 hours. The resulting reaction mixture was poured into cold water and extracted with 100 ml of ether. The obtained extract was washed successively with a saturated sodium hydrogencarbonate solution and two portions of a saturated sodium chloride solution. After drying the organic layer with anhydrous magnesium sulfate, the solvent was distilled away under reduced pressure to give a yellow liquor. The product was further distilled under reduced pressure (bp: 87° to 88° C./37 mmHg) in an atmosphere of nitrogen gas to give 8.44 g. (yield: 56.8%) of the desired compound being a clear solution.

GC-MS (20 eV)m/e: 148($M^+$), 150($M+2$), 113, 86, 69(base peak), 41 and 27

REFERENCE EXAMPLE 2

(1-Chloroethyl)-3,3-dimethylacrylate

The procedure of Reference Example 1 was repeated except that 6.8 g of paraldehyde, 0.2 g (2 mmoles) of 96% zinc chloride and 18.5 g (0.156 mole) of 3,3-dimethylacryloyl chloride were employed, to give 21.54 g. (yield: 85%) of the desired compound being a clear solution.

Boiling point: 86° to 87° C./24 mmHg GC-MS (20 eV) m/e: 162 ($M^+$), 164 ($M+2$), 126, 100, 83 (base peak), 63, 55 and 29

REFERENCE EXAMPLE 3

(1-Chloroethyl)-2,4-hexadienoate

A mixture of 5.6 g. (50 mmoles) of sorbic acid and 7.8 g. (65 mmoles) of thionyl chloride was stirred at a room temperature for one hour, and then reacted at 50° C. for 30 minutes with stirring to complete the reaction. The end point of the reaction was judged by cessation of $SO_2$ gas production and disappearance (dissolution) of sorbic acid. The resulting reaction mixture was cooled with ice, and then 0.27 g. (2 mmoles) of 96% zinc chloride was added thereto. After adding dropwise 2.2 g. of paraldehyde at 0° C., the reaction was carried out at a room temperature for one hour. The resulting reaction mixture was treated and purified in the same manner as in Reference Example 1 to give 5.43 g. (yield: 64.2%) of the desired compound being a clear solution.

Boiling point: 111° to 112° C./18 mmHg GC-MS (20 eV) m/e: 175 ($M^+$), 176 ($M+2$), 111, 97, 95(base peak), 67 and 41

EXAMPLE 1

1-(Acetoxy)ethyl 2-(2-fluoro-4-biphenylyl)propionate (Compound No. 1)

In 20 ml. of anhydrous dimethylformamide (hereinafter referred to as "DMF") was dissolved 2.44 g. (10 mmoles) of FP. To the resulting solution was added 1.38 g. (10 mmoles) of anhydrous potassium carbonate, and then the reaction mixture was stirred at a room temperature for 30 minutes. After adding dropwise 1.45 g. (12 mmoles) of (1-chloroethyl)acetate purified by distillation at 0° to 5° C., the reaction was carried out at 60° to 70° C. for one hour with stirring.

After completion of the reaction, the reaction mixture was cooled with ice, and then the inorganic material was filtered off. After distilling away the solvent under reduced pressure, 50 ml. of diethyl ether was added to the obtained residue. The resulting mixture was washed successively with water, 10% sodium carbonate solution and a saturated sodium chloride solution, and then the organic layer was dried with anhydrous magnesium sulfate. The solvent was distilled away under reduced pressure to give 2.97 g. (crude yield: 90%) of light yellowish oily material.

The resulting product was further distilled under reduced pressure in an atmosphere of nitrogen gas to give 2.4 g. (yield: 74%) of the desired compound being a clear oily material having a boiling point of 173° to 174° C./0.8 mmHg.

Elementary analysis for $C_{19}H_{19}FO_4$ (MW: 330): Calcd. (%): C 69.09 H 5.76 Found (%): C 69.16 H 5.89

Nuclear magnetic resonance spectrum (in $CCl_4$, TMS), δ(ppm):

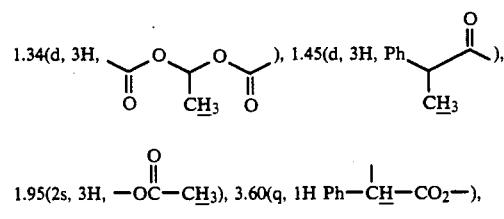

1.95(2s, 3H, —OC̲—CH₃), 3.60(q, 1H Ph—CH̲—CO₂—), 6.68 to 6.89(2q, 1H, —COO—CH̲—OC̲—) and 6.90 to 7.43(m, 8H, aromatic Mass spectrum (20 eV, Direct) m/e:

330(M.⁺), 244(M-CH(CH₃)OCCH₃)⁺,

226(M-OCH(CH₃)OCCH₃)⁺, 119[base peak,

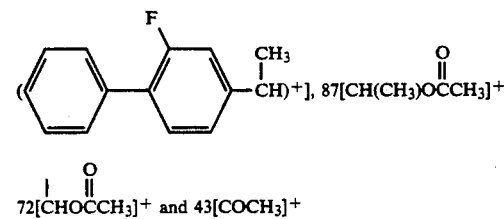

72[CHOC̲CH₃]⁺ and 43[COCH₃]⁺

Infrared absorption spectrum (νcm.⁻¹): 3060 to 2875 (aromatic, alkyl, νC—H), 1770 (νC═O ester) and 1630 (aromatic νC═C)

Refractive index: $n_D^{24.5} = 1.5353$

Ultraviolet absorption: λmax=247 nm.

EXAMPLE 2

1-(Propionyloxy)ethyl 2-(2-fluoro-4-biphenylyl)propionate (Compound No. 2)

The procedure of Example 1 was repeated except that 1.30 g. (10 mmoles) of (1-chloroethyl)propionate instead of (1-chloroethyl)acetate was employed to give 2.5 g. (yield: 73%) of the desired compound being a clear oily material.

Elementary analysis for $C_{20}H_{21}FO_4$ (MW: 344): Calcd. (%): C 69.77 H 6.10 Found (%): C 69.97 H 6.12

Nuclear magnetic resonance spectrum (in $CCl_4$, TMS), δ(ppm):

1.02 and 1.10(2t, 3H, —COCH₂CH₃), 1.34(d, 3H,

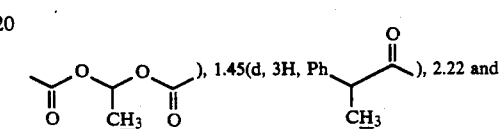

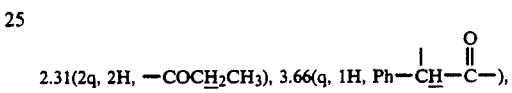

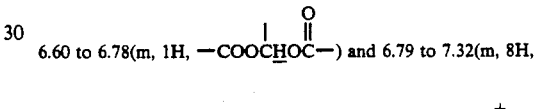

6.60 to 6.78(m, 1H, —COOCH̲OC—) and 6.79 to 7.32(m, 8H, aromatic H) Mass spectrum (20 eV, Direct) m/e: 344 (M.⁺), 226[M-OCH(CH₃)OC̲—C₂H₅]⁺, 199[base peak,

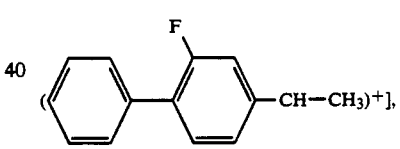

101[CH(CH₃)OC̲—C₂H₅]⁺, 57[COC₂H₅]⁺ and 29[C₂H₅]⁺

Infrared absorption spectrum (νcm.⁻¹): 3060 to 2875 cm.⁻¹ (aromatic, alkyl νC—H), 1760 (νC═O ester) and 1630 (aromatic νC═C)

Refractive index $n_D^{24.5} = 1.5331$

Ultraviolet absorption λmax=247 nm.

Boiling point: 188° to 191° C./0.4 mmHg

EXAMPLE 3

1-(Isobutyryloxyethyl) 2-(2-fluoro-4-biphenylyl)propionate (Compound No. 3)

The procedure of Example 1 was repeated except that 1.50 g. (10 mmoles) of (1-chloroethyl)isobutylate instead of 1-chloroethyl acetate was employed to give 2.72 g. (yield: 76%) of the desired compound being a clear oily material.

Elementary analysis for $C_{21}H_{23}FO_4$ (MW:358): Calcd. (%): C 70.39 H 6.42 Found (%): C 70.57 H 6.44

Nuclear magnetic resonance spectrum (in $CCl_4$, TMS), δ(ppm):

1.14(2d, 6H, —CH(C<u>H</u>₃)₂, 1.39 to 1.54(m, 6H, Ph<img>, 2.46(m, 1H —C<u>H</u>(CH₃/CH₃) ), 3.64 and 3.67(2q, 1H, Ph—C<u>H</u>—C(=O)—), 6.61 to 6.31(m, 1H, —COOC<u>H</u>OC—), 6.95 to 7.43(m, 8H, aromatic H) Mass spectrum (20 eV, Direct)

m/e: 358(M.⁺), 226[M-OCH(CH₃)OC(=O)—CH(CH₃)₂]⁺,

199[base peak, 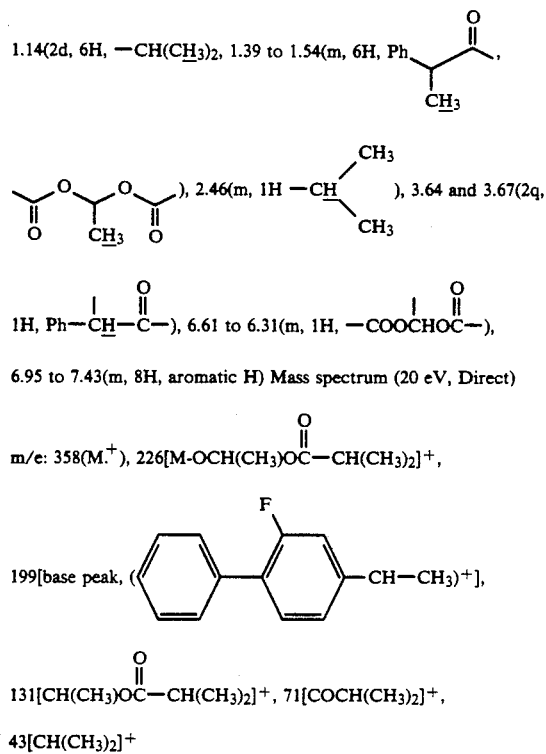 —CH—CH₃)⁺],

131[CH(CH₃)OC(=O)—CH(CH₃)₂]⁺, 71[COCH(CH₃)₂]⁺,

43[CH(CH₃)₂]⁺

Infrared absorption spectrum ($\nu$cm.⁻¹): 3060 to 2875 (aromatic, alkyl $\nu$C—H), 1760 ($\nu$C=O ester) and 1630 (aromatic $\nu$C=C)

Refractive index: $n_D^{24.5}$ = 1.5267
Ultraviolet absorption: $\lambda$max = 247 nm.
Boiling point: 160° to 164° C./0.5 mmHg

EXAMPLE 4

[1-(Pivaloyloxy)ethyl 2-(2-fluoro-4-biphenyl)propionate (Compound No. 4)]

The procedure of Example 1 was repeated except that 2.1 g. (13 mmoles) of (1-chloroethyl) 2,2-dimethyl propionate instead of (1-chloroethyl)acetate was employed to give 2.1 g. (yield: 56%) of the desired compound being a clear oily material.

Elementary analysis for C₂₂H₂₅FO₄ (MW: 372): Calcd. (%): C 70.97 H 6.72 Found (%): C 71.18 H 6.68

Nuclear magnetic resonance spectrum (in CCl₄, TMS), δ(ppm):

1.14(2s, 9H, —C(C<u>H</u>₃)₃, 1.39 to 1.54(2d, 6H, Ph<img>, 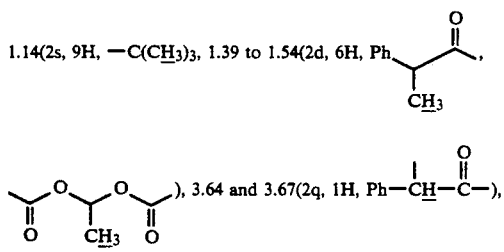), 3.64 and 3.67(2q, 1H, Ph—C<u>H</u>—C(=O)—), 6.61 to 6.81(m, 1H, —COOC<u>H</u>OC—), 6.95 to 7.43(m, 8H, aromatic H) Mass spectrum (20 eV, Direct) m/e: 372(M.⁺), 226[M-OCH(CH₃)OC(=O)—C(CH₃)₃], 199[base peak,

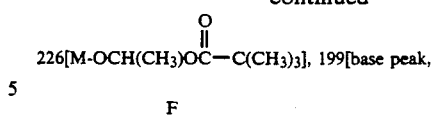—CH—CH₃)⁺],

129[CH(CH₃)OC(=O)—C(CH₃)₃]⁺, 85[COC(CH₃)₃]⁺, 57[C(CH₃)₃]⁺

Infrared absorption spectrum ($\nu$cm.⁻¹): 3060 to 2875 (aromatic, alkyl $\nu$C—H), 1760 ($\nu$C=O ester), 1630 (aromatic $\nu$C=C)

Refractive index: $n_D^{24.5}$ = 1.5203
Ultraviolet absorption: $\lambda$max = 247 nm.
Boiling point: 166° to 172° C./0.55 mmHg

EXAMPLE 5

[1-(Palmitoyloxy)ethyl 2-(2-fluoro-4-biphenylyl)propionate (Compound No. 5)]

The procedure of Example 1 was repeated except that 3.18 g. (10 mmoles) of (1-chloroethyl)palmitate instead of (1-chloroethyl)acetate was employed to give 3.1 g. of clear oily material. The obtained product was purified by chromatography on silica gel [Kiesel gel 60 made by Merck & Co., Inc. (60 g.); Eluent: (1) cyclohexane, (2) cyclohexane: dichloromethane=8:2, (3) cyclohexane: dichloromethane=6:4] to give 2.67 g. (yield: 50.7%) of the desired compound being a clear oily material.

Elementary analysis for C₃₃H₄₇FO₄ (MW: 326): Calcd. (%): C 75.29 H 8.94 Found (%): C 75.51 H 8.97

Nuclear magnetic resonance spectrum (in CCl₄, TMS), δ(ppm):

0.83 to 1.72(m, 35H, alkyl H), 2.18(t, 2H, —OC(=O)—C<u>H</u>₂—CH₂—), 3.69(q, 1H, Ph—C<u>H</u>—C(=O)—), 6.68 to 6.86(m, 1H, —COOC<u>H</u>OC(=O)—) and 6.98 to 7.52(m, 3H, aromatic H) Mass spectrum (20 eV, Direct) m/e: 526(M.⁺), 239[base peak, (CO(CH₂)₁₄CH₃)⁺] and 199[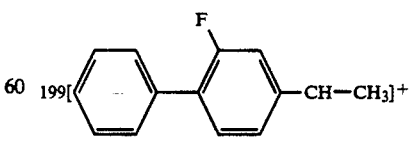—CH—CH₃]⁺

Infrared absorption spectrum ($\nu$cm.⁻¹): 3075 to 2875 (aromatic, alkyl $\nu$C—H), 1770 ($\nu$C=O ester), 1630 (aromatic $\nu$C=C)

Refractive index: $n_D^{24.5}$ = 1.5028
Ultraviolet absorption: $\lambda$max = 247 nm.

EXAMPLE 6

[1-(Crotonoyloxy)ethyl 2-(2-fluoro-4-biphenylyl)propionate (Compound No. 7)]

The procedure of Example 1 was repeated except that 1.38 g. (10 mmoles) of (1-chloroethyl)crotonate purified by distillation instead of (1-chloroethyl) acetate was employed to give 1.6 g. (yield: 44.9%) of the desired compound being a clear oily material.

Elementary analysis for $C_{21}H_{21}FO_4$ (MW: 356): Calcd. (%): C 70.79 H 5.90 Found (%): C 71.00 H 5.93

Nuclear magnetic resonance spectrum (in $CCl_4$, TMS), δ(ppm):

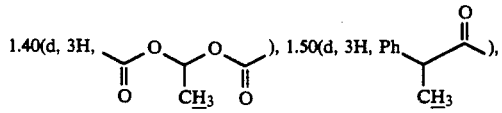

1.73 to 1.87(m, 3H, —CH=CH—C$\underline{H}_3$). 3.66(q, 1H,

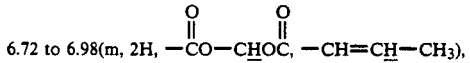

Ph—C$\underline{H}$—C—), 5.58 to 5.86(m, 1H, —C$\underline{H}$=CH—CH$_3$),

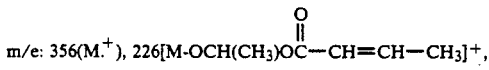

6.72 to 6.98(m, 2H, —CO—C$\underline{H}$OC, —CH=C$\underline{H}$—CH$_3$), 7.02 to 7.40 (m, 8H, aromatic H) Mass spectrum (20 eV, Direct)

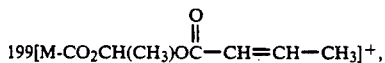

m/e: 356(M.$^+$), 226[M-OCH(CH$_3$)OC—CH=CH—CH$_3$]$^+$,

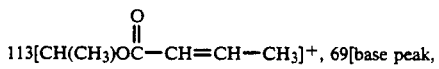

199[M-CO$_2$CH(CH$_3$)OC—CH=CH—CH$_3$]$^+$,

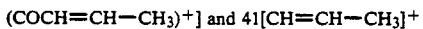

113[CH(CH$_3$)OC—CH=CH—CH$_3$]$^+$, 69[base peak, (COCH=CH—CH$_3$)$^+$] and 41[CH=CH—CH$_3$]$^+$ Infrared absorption spectrum (νcm.$^{-1}$): 3100 to 2900 (aromatic, alkyl νC—H), 1750 (νC=O ester) and 1665 (νC=C di-substituted olefine)

Refractive index: $n_D^{24.5} = 1.5397$

Ultraviolet absorption: λmax=247 mn. and 206 mn.

Boiling point: 195° to 197° C./0.3 mmHg

EXAMPLE 7

[[1-(3,3-dimethylacryloyloxy)ethyl]2-(2-fluoro-4-biphenylyl)propionate (Compound No. 8)]

The procedure of Example 1 was repeated except that 2.43 g. (15 mmoles) of (1-chloroethyl)-3,3-dimethylacrylate purified by distillation instead of (1-chloroethyl)acetate was employed to give 3.19 g. (yield: 85.1%) of the desired compound being a clear oily material.

Elementary analysis for $C_{22}H_{23}FO_4$ (MW: 370): Calcd. (%): C 71.35 H 6.22 Found (%): C 71.14 H 6.21

Nuclear magnetic resonance spectrum (in $CCl_4$, TMS), δ(ppm):

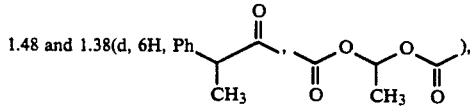

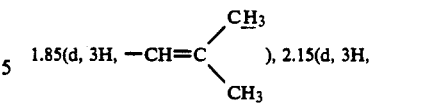

1.85(d, 3H, —CH=C(CH$_3$)(CH$_3$)), 2.15(d, 3H,

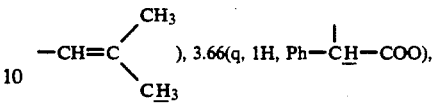

—CH=C(CH$_3$)(CH$_3$)), 3.66(q, 1H, Ph—C$\underline{H}$—COO), 5.46 to 5.60(m, 1H, olefinic H), 6.69 to 6.89(2q, 1H,

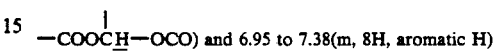

—COOC$\underline{H}$—OCO) and 6.95 to 7.38(m, 8H, aromatic H)

Mass spectrum (20 eV, Direct) m/e:

370(M.$^+$), 226[M—OCH(CH$_3$)OC—CH=C(CH$_3$)$_2$]$^+$,

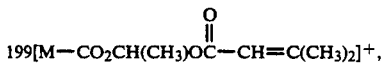

199[M—CO$_2$CH(CH$_3$)OC—CH=C(CH$_3$)$_2$]$^+$,

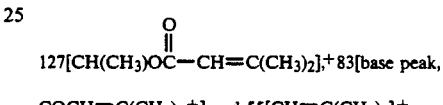

127[CH(CH$_3$)OC—CH=C(CH$_3$)$_2$]$^+$, 83[base peak,

COCH=C(CH$_3$)$_2$$^+$] and 55[CH=C(CH$_3$)$_2$]$^+$

Infrared absorption spectrum (νcm.$^{-1}$): 3075 to 2900 (aromatic, alkyl νC—H), 1750 (νC=O ester), 1660 (νC=C, tri-substituted olefine)

Refractive index: $n_D^{24.5} = 1.5423$

Ultraviolet absorption: λmax=244 nm. and 206 nm.

Boiling point: 194° C./0.6 mmHg

EXAMPLE 8

[1-(2,4-Hexadienoyloxy)ethyl]2-(2-fluoro-4-biphenylyl)propionate (Compound No. 9)]

The procedure of Example 5 was repeated except that 2.26 g. (13 mmoles) of (1-chloroethyl)-2,4-hexadienoate purified by distillation instead of (1-chloroethyl)palmitate was employed to give 3.17 g. (yield: 83.0%) of the desired compound being a clear oily material.

Elementary analysis for $C_{23}H_{23}FO_4$ (MW: 382): Calcd. (%): C 72.25 H 6.02 Found (%): C 72.47 H 6.04

Nuclear magnetic resonance spectrum (in $CCl_4$, TMS), δ(ppm):

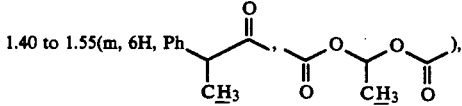

1.77 to 1.89(m, 3H, —CH=CH—C$\underline{H}_3$),

3.69(q, 1H, Ph—C$\underline{H}$—CO$_2$), 5.54 to 5.79(2d, 2H, olefinic H), 6.03 to 6.20(m, 1H, olefinic H),

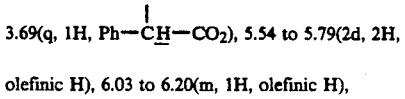

6.75 to 6.93(m, 2H, olefinic H, —COOC$\underline{H}$OC—), 7.00 to 7.46(m, 8H, aromatic H)

-continued

Mass spectrum (20 eV, Direct) m/e:

382(M.+),

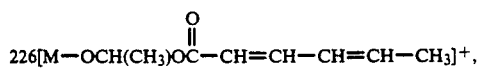
226[M—OCH(CH$_3$)OC(=O)—CH=CH—CH=CH—CH$_3$]+,

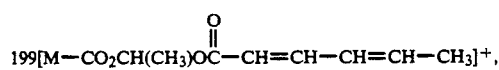
199[M—CO$_2$CH(CH$_3$)OC(=O)—CH=CH—CH=CH—CH$_3$]+,

95[base peak, (COCH=CH—CH=CH—CH$_3$)+] and

67[CH=CH—CH=CH—CH$_3$]+

Infrared absorption spectrum ($\nu$cm.$^{-1}$): 3075 to 2875 (aromatic, alkyl $\nu$C—H), 1755 ($\nu$C=O ester), 1652 (olefinic $\nu$C=C)

Refractive index: $n_D^{24.5}$ = 1.5612

Ultraviolet adsorption: $\lambda$max = 254 nm.

EXAMPLE 9

[1-(Acetoxy)propyl 2-(2-fluoro-4-biphenylyl)propionate (Compound No. 6)]

The procedure of Example 5 was repeated except that 1.4 g. (10 mmoles) of (1-chloropropyl)acetate purified by distillation instead of (1-chloroethyl) palmitate was employed to give 1.2 g. (yield: 34.8%) of the desired compound being a brown oily material.

Elementary analysis for C$_{20}$H$_{21}$FO$_4$ (MW: 344): Calcd. (%): C 69.77 H 6.10 Found (%): C 69.99 H 6.12

Nuclear magnetic resonance spectrum (in CCl$_4$, TMS), $\delta$(ppm):

0.72 to 1.00(m, 3H, —CHCH$_2$C$\underline{H}$$_3$),

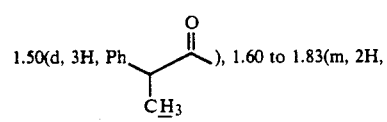
1.50(d, 3H, Ph\_\_\_\_), 1.60 to 1.83(m, 2H,

—CHC$\underline{H}$$_2$CH$_3$), 1.95(2s, 3H, —OCOC$\underline{H}$$_3$), 3.66(q,

1H, Ph—C$\underline{H}$—COO), 6.49 to 6.66(m, 1H, —COOC$\underline{H}$OC(=O)—), 6.95 to 7.35(m, 8H, aromatic H)

Mass spectrum (20 eV, Direct) m/e:

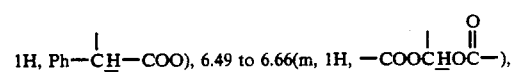
344(M.+), 199[...—CH—CH$_3$]+,

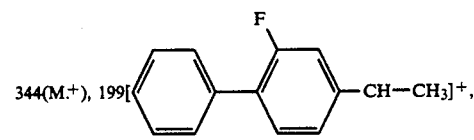
101[CH(C$_2$H$_5$)OC(=O)—CH$_3$]+ and 43[COCH$_3$]+

Infrared absorption spectrum ($\nu$cm.$^{-1}$): 3080 to 2900 (aromatic, alkyl $\nu$C—H), 1770 ($\nu$C=O ester), 1632 (aromatic $\nu$C=C)

Refractive index: $n_D^{24.5}$ = 1.5310

Ultraviolet absorption: $\lambda$max = 247 nm.

EXAMPLE 10

[1-(Acetoxy)ethyl 2-(2-fluoro-4-biphenylyl)propionate (Compound No. 1)]

Into 140 ml. of anhydrous DMF was suspended 2.82 g. (10 mmoles) of potassium salt of FP. To the resulting suspension was added dropwise 1.47 g. (12 mmoles) of (1-chloroethyl)acetate dissolved in 10 ml. of anhydrous DMF while keeping the reaction mixture at a temperature of 60° C., and then the resulting reaction mixture was stirred at 80° C. for one hour. After completion of the reaction, the resulting reaction mixture was treated and purified in the same manner as in Example 1 to give 2.5 g. (yield: 75%) of the desired compound being a clear oily material.

The physicochemical properties of the compound were consistent with those obtained in Example 9.

EXAMPLE 11

1-(Propionyloxy)ethyl 2-(2-fluoro-4-biphenylyl)propionate (Compound No. 2)

To 30 ml. of dehydrated acetonitrile were added 0.84 g. (3 mmoles) of potassium salt of FP, 0.3 g. (3 mmoles) of triethylamine and 0.5 g. (3 mmoles) of potassium iodide.

To the resulting reaction mixture was added 0.47 g. (4 mmoles) of (1-chloroethyl)propionate at a room temperature with stirring, and then the reaction was carried out at 60° C. for 5 hours. After cooling, the resulting residue was filtered off, and then 100 ml. of ether was added to the filtrate. The resulting organic layer was washed successively with 10% sodium carbonate solution, water and a saturated sodium chloride aqueous solution by a conventional method, and then dried with magnesium sulfate. After distilling away the solvent, the obtained oily material was distilled under reduced pressure to give 0.84 g. (yield: 83%) of the desired compound. The physicochemical properties of the compound were consistent with those obtained in Example 2.

EXAMPLE 12

1-(Pivaloyloxy)ethyl 2-(2-fluoro-4-biphenylyl)propionate (Compound No. 4)

To 40 ml. of dehydrated acetonitrile was added 20 mg. of 18-crown-6, and then the resulting reaction mixture was stirred at a room temperature for 30 minutes. To the resulting reaction mixture were added 0.56 g. (2 mmoles) of potassium salt of FP and then 0.49 g. (3 mmoles) of (1-chloroethyl) 2,2-dimethylpropionate, and the reaction was carried out at 50° C. for 8 hours. After cooling and adding 100 ml. of ether, the resulting reaction mixture was treated and purified in the same manner as in Example 4 to give 0.37 g. (yield: 50%) of the desired compound. The physicochemical properties of the compound were consistent with those obtained in Example 12.

EXAMPLE 13

1-(Acetoxy)ethyl 2-(2-fluoro-4-biphenylyl)propionate (Compound No. 1)

In 25 ml. of acetonitrile was dissolved 2.44 g. (10 mmoles) of FP. To the resulting solution was added 1.38 g. (10 mmoles) of anhydrous potassium carbonate, and then the reaction mixture was stirred at a room temperature for 30 minutes. After adding dropwise 2.4 g. (20 mmoles) of (1-chloroethyl)acetate purified by distillation, the reaction was carried out at a room temperature for 4 hours, and then at 40° C. for one hour with stirring. After cooling, the resulting residue was filtered off, and 100 ml. of ether was added to the filtrate. The resulting organic layer was washed successively with 10% sodium carbonate solution, water and a saturated sodium chloride aqueous solution, and then dried with magnesium sulfate. After distilling away the solvent, the obtained oily material was distilled under reduced pressure to give 2.3 g. (yield: 71%) of the desired compound. The physicochemical properties of the compound were consistent with those obtained in Example 1.

EXAMPLE 14

1-(Acetoxy)ethyl 2-(2-fluoro-4-biphenyl)propionate (Compound No. 1)

The procedure of Example 1 was repeated except that 1.67 g. (10 mmoles) of (1-bromoethyl)acetate instead of (1-chloroethyl)acetate was employed to give 2.56 g. (yield: 81%) of the desired compound being a clear oily material. The physicochemical properties of the compound were consistent with those obtained in Example 1.

EXAMPLE 15

3,3-Dimethyl-2-[2-(2-fluoro-4-biphenylyl)propionyloxy]-γ-butyrolactone (Compound No. 10)

In 40 ml. of anhydrous dichloromethane were dissolved 2.44 g. (10 mmoles) of FP, 1.3 g. (10 mmoles) of 2-hydroxy-3,3-dimethylbutyrolactone and 0.1 g. of p-dimethylaminopyridine. To the resulting solution was added dropwise 2.0 g. (10 mmoles) of dicyclohexylcarbodiimide, and the resulting reaction mixture was stirred at a room temperature for one hour. After completion of the reaction, the reaction mixture was cooled to a temperature of 0° C., and the precipitated dicyclohexylurea was filtered off. The resulting filtrate was washed successively with 0.1N hydrochloride, a saturated sodium bicarbonate solution and a saturated sodium chloride solution, and then the organic layer was dried with anhydrous magnesium sulfate. After distilling away the solvent under reduced pressure, the resulting light yellowish liquor was distilled under reduced pressure for purification to give 2.41 g. (yield: 68%) of the desired compound being an oily material having a boiling point of 198° to 209° C./0.9 mmHg.

Elementary analysis $C_{21}H_{21}FO_4$ (MW: 356): Calcd. (%): C 70.79 H 5.90 Found (%): C 70.93 H 5.92

Nuclear magnetic resonance spectrum (in $CCl_4$, TMS), δ(ppm):

0.86 to 1.17(s × 4, 6H, lactone $C\underline{H}_3$ × 2),

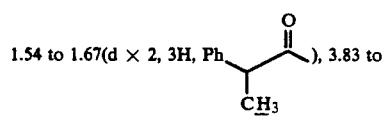

1.54 to 1.67(d × 2, 3H, Ph...), 3.83 to 3.96(m, 3H, PhC$\underline{H}$COO, —CO$_2$C$\underline{H}_2$—$\underline{C}$—), 5.26 to 5.30(s × 2, 1H, —COOC$\underline{H}$—COO) and 7.08 to 7.43(m, 8H, aromatic H)

Mass spectrum (20 eV, Direct) m/e:

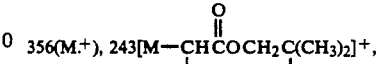

356(M.+), 243[M—CHCOCH$_2$C(CH$_3$)$_2$]+,

226[M—OCHCOCH$_2$C(CH$_3$)$_2$]+ and

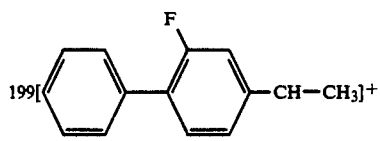

199[...—CH—CH$_3$]+

Infrared absorption spectrum ($\nu cm^{-1}$): 3100 to 2900 (aromatic, alkyl, C—H), 1760 ($\nu$C=O ester) and 1800 (γ-lactone $\nu$C=O)

Refractive index: $n_D^{24.5}$ = 1.5485
Ultraviolet absorption: λmax = 247 nm

EXAMPLE 16

3,3-Dimethyl-2-[2-(2-fluoro-4-biphenyly)propionyloxy]-γ-butyrolactone (Compound No. 10)

In 50 ml. of anhydrous tetrahydrofuran were dissolved 2.44 g. (10 mmoles) of FP, 1.3 g. (10 mmoles) of D,L-pantolactone and 2.6 g. of triphenylphosphin. After adding dropwise 1.7 g. (10 mmoles) of azocarboxylic acid diethyl ester with stirring at 0° C., the reaction was carried out at 0° C. for one hour, and then at a room temperature for one hour. After adding 20 ml. of ether to the reaction mixture, the resulting precipitate was filtered off. The resulting organic layer was washed three times with water, and then dried with anhydrous magnesium sulfate. After distilling away the solvent, the obtained residue was distilled under reduced pressure for purification to give 2.3 g. (yield: 65%) of the desired compound being a clear oily material.

The physicochemical properties of the obtained compound were consistent with those obtained in Example 15.

EXAMPLE 17

3,3-Dimethyl-2-[2-(2-fluoro-4-biphenylyl)propionyloxy]-γ-butyrolactone (Compound No. 10)

In 10 ml. of anhydrous DMF was dissolved 2.44 g. (10 mmoles) of FP in an atmosphere replaced with argon gas. After adding dropwise N,N'-carbonyldiimidazole dissolved in anhydrous DMF at a room temperature, the reaction was carried out for one hour with stirring. To the resulting reaction mixture was added dropwise 1.3 g. (10 mmoles) of D,L-pantolactone with ice-cooling. After completion of the addition, the reaction was carried out at a room temperature for 3 hours with stirring. The resulting reaction mixture was concentrated under reduced pressure, and then the residue was dissolved in ether. The resulting mixture was washed successively with water, 10% citric acid, water, a saturated sodium bicarbonate solution and a saturated sodium chloride solution, and then the organic layer was dried with anhydrous magnesium sulfate. After distilling away the solvent under reduced pressure, the obtained residue was distilled under reduced pressure for purification to give 2.5 g. (yield: 71%) of the desired compound being a clear oily material.

The physicochemical properties of the obtained compound were consistent with those obtained in Example 15.

EXAMPLE 18

Tablet

To 100 mg. of 1-(acetoxy)ethyl 2-(2-fluoro-4-biphenylyl)propionate was added 30 mg. of Aerosil (registered trademark, made by Japan Aerosil Co., Ltd.), and the mixture was pulverized. To the resulting powder were added 35 mg. of dibasic calcium phosphate anhydrous, 45 mg. of Avicel (registered trademark, made by Ashahi Kasei Co., Ltd.), 6 mg. of ECG 505 (carboxymethyl cellulose calcium salt made by Nichirin Chemical Industry Co., Ltd.) and 4 mg. of calcium stearate, and then the mixture was blended and compressed to give a tablet.

EXAMPLE 19

Suppository

A mixture of 1240 mg. of Witepsol H-15 (mixture of triglyceride and monoglyceride made by Dinamit Novel Co., Ltd., Witepsol: registered trademark) and 310 mg. of Witepsol E-85 (made by Dinamit Nobel Co., Ltd.) was melted at 60° to 70° C. After cooling the mixture to a temperature of 45° C., 150 mg. of 1-(acetoxy)ethyl 2-(2-fluoro-4-biphenylyl) propionate was added thereto. The resulting mixture was stirred until it became homogeneous, and then 1.7 g. thereof was injected in a container of 1.9 ml. at 40° C. to make solid with cooling.

EXAMPLE 20

Soft gelatin capsule (a) For oral administration

In 100 mg. of PEG 400 (polyethyleneglycol) was dissolved 100 mg. of 1-(acetoxy)ethyl 2-(2-fluoro-4-biphenylyl)propionate, and then 200 mg. of the resulting solution was filled up in a soft gelatin capsule (made by R. P. Scherer Co., Ltd.; size: 3 to 2 round A).

(b) For Suppositories

In 260 mg. of PEG 400 was dissolved 150 mg. of 1-(acetoxy)ethyl 2-(2-fluoro-4-biphenylyl)propionate, and then 410 mg. of the resulting solution was filled up in a soft gelatin capsule (made by R. P. Scherer Co., Ltd.; size: 85 to 86 suppository A).

EXAMPLE 21

Cream

According to the following formulation, a 1% gel cream was prepared as follows:

| | |
|---|---|
| 1-(Acetoxy)ethyl 2-(2-fluoro-4-biphenylyl) propionate | 10 g. |
| Myristin isopropyl (made by Nikko Chemicals Co., Ltd.) | 100 g. |
| Ethanol | 50 g. |
| Polyoxyethylene monostearate | 10 g. |
| Carboxyvinyl polymer-940 | 15 g. |
| Coconut oil (fatty acid diethanol amide) | 30 g. |
| Distilled water | Sufficient amount |
| Total | 1000 g. |

In myristin isopropyl was dissolved 1-(acetoxy)ethyl 2-(2-fluoro-4-biphenylyl)propionate. To the resulting solution were added ethanol, carboxyvinyl polymer-940 swelled in 500 ml. of water and polyoxyethylene dissolved in 100 ml. of water, and then the resulting mixture was throughly stirred until it became homogeneous. To the homogeneous mixture were added coconut oil blended in 100 ml. of water and sufficient amount of distilled water, and then the resulting mixture was throughly stirred until it became homogeneous.

EXAMPLE 22

Inhibitory effect on carrageenan-induced edema

With respect to the present FP derivatives (Compound Nos. 1 to 10), there was tested inhibitory effect on carrageenan-induced edema.

Five Wistar male rats weighing about 150 g. were used as one group. A 1% dispersion of carrageenan was injected intracutaneously into the foot pad of the right hind foot in a dose of 0.1 ml./rat. The compounds to be tested were orally administered to the rats fasted for 15 hours one hour before the carrageenan injection, or intravenously administered 2 hours after the carrageenan injection. The volume of the foot subjected to the injection was measured by a mercury plethysmography 3 hours after the carrageenan injection on the test by oral route or 2 hours after the carrageenan injection on the test by intravenous route, and the carrageenan-induced edema was estimated from the obtained measurements. The results are shown in Table 2.

TABLE 2

| | Compound No. | $ED_{50}$ mg./kg. | |
|---|---|---|---|
| | | p.o. | i.v. |
| Compounds of the invention | 1 | 0.5 | 0.05 |
| | 2 | 0.7 | 0.06 |
| | 3 | 1.5 | 0.1 |
| | 4 | 2.5 | 0.6 |
| | 5 | >5.0 | >5.0 |
| | 6 | 1.5 | 0.1 |
| | 7 | 0.9 | 0.08 |
| | 8 | 2.5 | 0.3 |
| | 9 | 2.0 | 0.3 |
| | 10 | 0.5 | 0.05 |
| Comparative compounds | acemethacin | 8.3 | — |
| | indomethacin | 5.5 | 1.25 |
| | FP | 0.8 | 0.3 |

EXAMPLE 23

Gastric ulceration

With respect to the present FP derivatives (Compound Nos. 1 to 10), there was tested gastric ulceration.

Five Wistar male rats weighing about 150 g. were used as one group. The rats were fasted for 24 hours before the test.

Six hours after orally administration of the compounds to be tested, there was observed an existence of gastric ulcer by the method of Okabe et al (Ohyoyakuri, 16, 241 to 247 (1978)). The $UD_{50}$ values were calculated from the ulcer incidence of gastric ulcer by the method of Litchfield-Wilcoxon. The results are shown in Table 3.

TABLE 3

| | Compound No. | $UD_{50}$ mg./kg. |
|---|---|---|
| Compounds of the | 1 | 2.5 |
| | 2 | 3.0 |

TABLE 3-continued

| | Compound No. | UD$_{50}$ mg./kg. |
|---|---|---|
| invention | 3 | 5.0 |
| | 4 | 10.0 |
| | 5 | >10.0 |
| | 6 | 5.0 |
| | 7 | 4.0 |
| | 8 | 7.0 |
| | 9 | 7.0 |
| | 10 | 2.5 |
| Comparative compounds | acemethacin | 17.5 |
| | indomethacin | 5.0 |
| | FP | 1.0 |

EXAMPLE 24

Hydrolysis of FP derivatives in plasma

With respect to the present FP derivatives (Compound Nos. 1 to 10), there was tested the hydrolysis rate in human plasma or rat plasma.

The compounds to be tested (Compound Nos. 1 to 9) and the compound to be tested (Compound No. 10) were, respectively, added to 1 ml. of human plasma and 1 ml. of rat plasma, in an amount corresponding to 50 μg. of FP. Each reaction mixture was incubated at 37° C. for one hour.

The free FP formed by esterase in the plasma was extracted with benzene. After treating the extract with N,O-bis(trimethylsilylacetamide) for trimethylsilylation, the obtained material was determined by gas-liquid chromatography. The results are shown in Table 4.

TABLE 4

| | Compound No. | Hydrolyzing rate (%) |
|---|---|---|
| Compounds of the invention | 1 | 70.7 |
| | 2 | 56.3 |
| | 3 | 35.2 |
| | 4 | 8.3 |
| | 5 | 2.0 |
| | 6 | 36.0 |
| | 7 | 42.0 |
| | 8 | 19.8 |
| | 9 | 20.4 |
| | 10 | 72.3 |
| Comparative compounds | acemethacin | 4.2 |
| | indomethacin | — |
| | FP | — |

EXAMPLE 25

Acute toxicity

Eight male SLC-ddY mice 5 week old weighing 25 to 30 g. were used as one group. The compound to be tested was orally administered using a stomach tube. The animals were kept under observation for 2 weeks. The numbers of dead animals were counted and the LD$_{50}$ values were calculated by the method of Litchfield Wilcoxon. The results are shown in Table 5.

TABLE 5

| | Compound No. | LD$_{50}$ mg./kg. |
|---|---|---|
| Compounds of the invention | 1 | 650 |
| | 2 | 800 |
| | 3 | 880 |
| | 4 | >1000 |
| | 5 | >1000 |
| | 6 | 900 |
| | 7 | 800 |
| | 8 | 1000 |
| | 9 | 1000 |
| | 10 | 670 |
| Comparative compounds | acemethacin | 18.0 |
| | indomethacin | 14.0 |
| | FP | 440 |

What we claim is:

1. A biphenylylpropionic acid derivative having the formula (I):

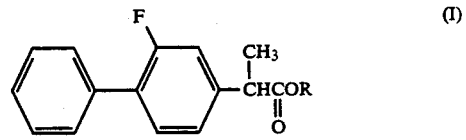

wherein R is 1-propionyloxyethyl, 1-isobutyryloxyethyl, 1-acetoxypropyl, or 1-crotonoyloxyethyl.

2. A pharmaceutical composition having anti-inflammatory, analgesic and antipyretic activities which comprises, an effective amount of a biphenylylpropionic acid derivative having the formula (I):

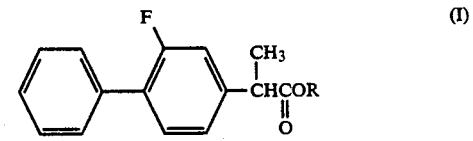

wherein R is 1-propionyloxyethyl, 1-isobutyryloxyethyl, 1acetoxypropyl, or 1-crotonoyloxyethyl., and a pharmaceutically acceptable carrier.

3. The pharmaceutical composition of claim 2, which is in the form of a tablet, a capsule, a suppository and a cream.

4. A method of treatment of inflammation, pain and fever in a mammal, which comprises administering to a mammal an anti-flammatory, analgesic and antipyretic effective amount of a compound according to claim 1 in combination with pharmaceutically acceptable carrier.

* * * * *